(12) United States Patent
Sato

(10) Patent No.: US 10,804,620 B2
(45) Date of Patent: Oct. 13, 2020

(54) IMAGING MODULE CAN EASILY AND STABLY CONNECT AN IMAGING-SENSING DEVICE TO A COAXIAL CABLE

(71) Applicant: FUJIKURA LTD., Tokyo (JP)

(72) Inventor: Takao Sato, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/392,764

(22) Filed: Apr. 24, 2019

(65) Prior Publication Data

US 2019/0348770 A1 Nov. 14, 2019

(30) Foreign Application Priority Data

May 9, 2018 (JP) .................................. 2018-090788

(51) Int. Cl.
*H01R 4/02* (2006.01)
*G02B 23/24* (2006.01)
*H01L 23/00* (2006.01)
*H01L 27/146* (2006.01)
(Continued)

(52) U.S. Cl.
CPC ......... *H01R 4/027* (2013.01); *G02B 23/2484* (2013.01); *H01L 24/32* (2013.01); *H01L 24/33* (2013.01); *H01R 4/023* (2013.01); *H01R 4/028* (2013.01); *H01R 43/0263* (2013.01); *H04N 5/2253* (2013.01); *H01L 27/14601* (2013.01); *H01L 2224/26135* (2013.01); *H01L 2224/26145* (2013.01); *H01L 2224/32225* (2013.01); *H01L 2224/32245* (2013.01); *H01L 2224/3313* (2013.01); *H01L 2224/3315* (2013.01)

(58) Field of Classification Search
CPC ... A61B 1/00163; A61B 1/00126; A61B 1/06; A61B 1/05; A61B 1/00096; A61B 1/00117; A61B 1/00009; G02B 23/2407; H04N 5/2257; H04N 2005/2255; H04N 5/374–37457; H01L 27/1464
USPC .......................................... 257/447; 348/308
See application file for complete search history.

(56) References Cited

U.S. PATENT DOCUMENTS

2014/0284751 A1 9/2014 Kamei
2016/0029879 A1 2/2016 Ishikawa
(Continued)

FOREIGN PATENT DOCUMENTS

CN 205720863 U 11/2016
JP 2000075218 A 3/2000
JP 2015-039410 A 3/2015
(Continued)

*Primary Examiner* — Xi Wang
(74) *Attorney, Agent, or Firm* — Osha Liang LLP

(57) ABSTRACT

An imaging module of the invention includes: an image-sensing device that has a light-receiving face, a terminal surface located on an opposite side of the light-receiving face, and a plurality of image-sensing terminals provided on the terminal surface; a support that has a first end disposed on the terminal surface, a second end disposed on an opposite side of the first end, a side face disposed between the first end and the second end, and a guide disposed on the side face so as to correspond to positions of the image-sensing terminals and that is formed of an insulator; a coaxial cable including a conductor disposed on the guide; and solder that electrically connects the conductor to an image-sensing terminal corresponding to the conductor on the guide.

9 Claims, 7 Drawing Sheets

(51) Int. Cl.
*H04N 5/225* (2006.01)
*H01R 43/02* (2006.01)

(56) References Cited

U.S. PATENT DOCUMENTS

2017/0251914 A1* 9/2017 Kitano ................... A61B 1/051
2018/0070803 A1* 3/2018 Mikami ............. A61B 1/00163

FOREIGN PATENT DOCUMENTS

| | | |
|---|---|---|
| JP | 2017018415 A | 1/2017 |
| JP | 2017099530 A | 6/2017 |
| JP | 2017099856 A | 6/2017 |
| JP | 2017108396 A | 6/2017 |
| JP | 2018038677 A | 3/2018 |
| WO | 2015019671 A1 | 2/2015 |
| WO | 2017199776 A1 | 11/2017 |

* cited by examiner

IMAGING MODULE CAN EASILY AND STABLY CONNECT AN IMAGING-SENSING DEVICE TO A COAXIAL CABLE

CROSS REFERENCE TO RELATED APPLICATIONS

This application claims priority from Japanese Patent Application No. 2018-090788 filed on May 9, 2018, the contents of which are incorporated herein by reference in their entirety.

TECHNICAL FIELD

The present invention relates to an imaging module.

BACKGROUND

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2017-18415).

In this kind of imaging module, ends of the electrical cable are electrically connected to a plurality of wirings of the wiring substrate, and each electrical cable is electrically connected to the image-sensing device via the wiring of the wiring substrate.

In recent years, an endoscope having a further small diameter is required, as an electrical cable used in a transmission path of the endoscope, an ultrafine electrical cable is employed. However, a pixel signal transmitted through the above-described electrical cable easily receives noise from the outside in the transmission path. Accordingly, it is necessary that a Micro ultrafine coaxial cable which is not a single electrical cable and is configured to include an internal conductor and an external conductor is used in the transmission path.

As a connection structure between the coaxial cable and the image-sensing device, a configuration may be considered in which a base body or a three-dimensional wiring substrate is not provided between the coaxial cable and the image-sensing device and in which the coaxial cable is directly soldered to the image-sensing device. In this case, it is necessary to separate one coaxial cable into an internal conductor and an external conductor and carry out operation of connecting the internal conductor and the external conductor which were separated therefrom to an extremely small image-sensing device. In this case, a level of difficulty of the connection operation is high, and it is difficult to economically manufacture imaging modules.

SUMMARY

One or more embodiments of an imaging module can easily and stably connect an image-sensing device to a coaxial cable.

An imaging module according to one or more embodiments of the invention includes: an image-sensing device that has a light-receiving face and a terminal surface located on an opposite side of the light-receiving face, and includes a plurality of image-sensing terminals provided on the terminal surface; a support that has a first end provided on the terminal surface, a second end located on an opposite side of the first end, and a side face located between the first end and the second end, includes a guide provided on the side face so as to correspond to positions of the image-sensing terminals, and is formed of an insulating member (insulator); a coaxial cable that includes a conductor disposed on the guide; and solder that electrically connects the conductor to an image-sensing terminal corresponding to the conductor on the guide.

In the imaging module according to one or more embodiments of the invention, the support may include a conductive portion provided on a surface of the guide, and, on the guide, the solder may electrically connect together the conductive portion, the image-sensing terminal corresponding to the conductor, and the conductor.

In the imaging module according to one or more embodiments of the invention, the guide of the support includes a plurality of grooves provided on the side face so as to correspond to positions of the image-sensing terminals, the conductor of the coaxial cable is disposed inside each of the plurality of grooves, in the inside of each of the plurality of grooves, the solder may electrically connect the conductor to one of the plurality of image-sensing terminals that corresponds to the conductor.

In the imaging module according to one or more embodiments of the invention, the support may include an end-face conductive portion that is provided on the second end and is electrically connected to the conductive portion, the end-face conductive portion may include: a connection portion between the conductive portion and the conductor; and an end portion located at a position separated from the connection portion, the solder may form a curved surface that extends from the end portion toward an outside of the second end along a surface of the conductor, and the solder may coat the end-face conductive portion and the connection portion.

In the imaging module according to one or more embodiments of the invention, the conductor may be an internal conductor of the coaxial cable, the coaxial cable may include an external conductor that covers an outside of the internal conductor, the internal conductor may be disposed inside a first groove of the plurality of grooves, the internal conductor may be electrically connected to an image-sensing terminal corresponding to the first groove, the external conductor may be disposed inside a second groove of the plurality of grooves, and the external conductor may be electrically connected to an image-sensing terminal corresponding to the second groove.

In the imaging module according to one or more embodiments of the invention, the first groove and the second groove may extend obliquely with respect to a center line orthogonal to the first end so as to be axisymmetric with respect to the center line, the internal conductor and the external conductor may be split from the coaxial cable in a Y-shape, the internal conductor may be disposed inside the first groove so as to extend along the first groove, and the external conductor may be disposed inside the second groove so as to extend along the second groove.

In the imaging module according to one or more embodiments of the invention, regarding the side face on which the first groove and the second groove are not provided, a width of the side face in a direction orthogonal to the center line gradually may decrease in a direction from the first end to the second end.

In the imaging module according to one or more embodiments of the invention, the support may be formed in a crisscross shape having four grooves in plan view, and each of the four grooves may function as the guide.

In the imaging module according to one or more embodiments of the invention, the support may be formed in an I-shape having a first side face and a second side face located on an opposite side of the first side face, in plan view, each of the first side face and the second side face may have a first region and a second region, and each of the first region and the second region may function as the guide.

In the imaging module according to one or more embodiments of the invention, on each of the first side face and the second side face, protrusion may be formed between the first region and the second region, and the protrusion may function as the guide.

As described above, according to the above-mentioned one or more embodiments of the invention, it is possible to provide an imaging module that can easily and stably connect an image-sensing device to a coaxial cable.

DETAILED DESCRIPTION OF THE INVENTION

Figure 1:
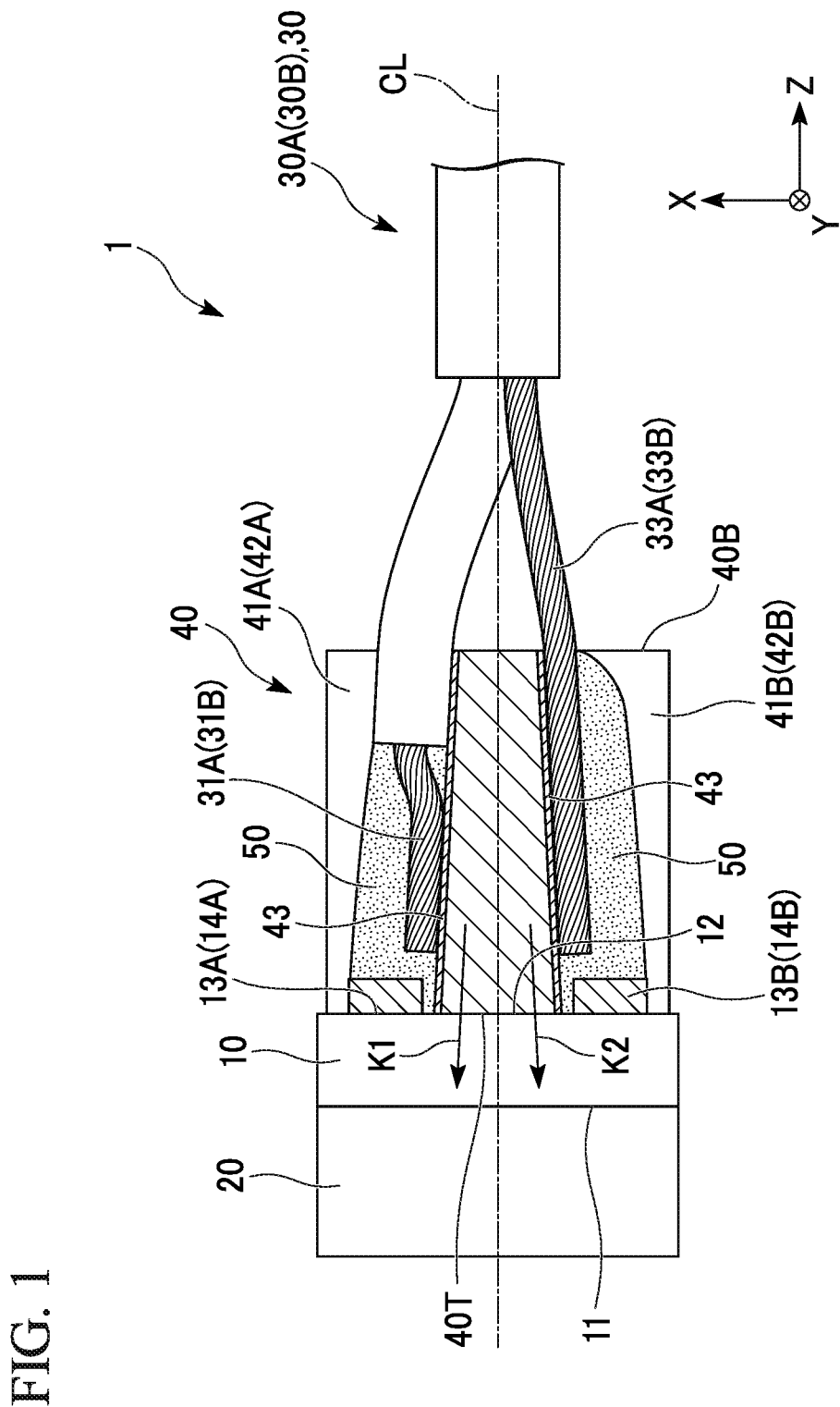
FIG. 1 is a cross-sectional view partially showing a schematic configuration of an imaging module according to one or more embodiments of the invention.

Hereinafter, embodiments of the invention will be described with reference to drawings.

In the drawings showing embodiments of the invention, in order for the respective components to be of understandable size in the drawings, the dimensions and the proportions of the components are modified as needed compared with the real components.

One or more embodiments of the invention will be described with reference to FIGS. 1 to 3.

Figure 2:
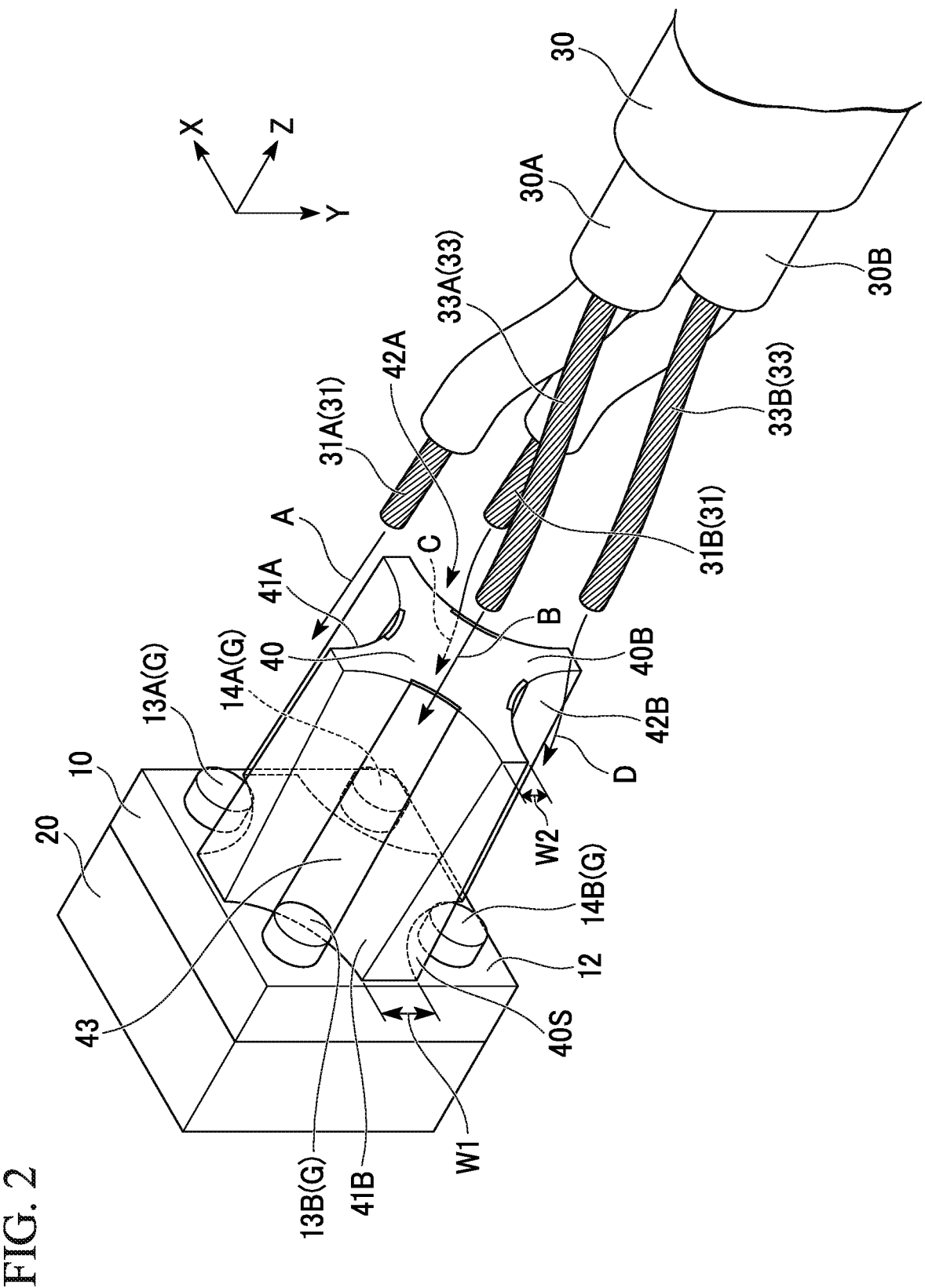
FIG. 2 is an enlarged perspective view showing a connection structure of a solid-state image sensing device, a support, and a coaxial cable which constitute the imaging module according to one or more embodiments of the invention and is a view showing a state before the coaxial cable is connected to the support.

As shown in FIGS. 1 and 2, an imaging module according to one or more embodiments of the invention 1 includes a solid-state image sensing device 10 (image-sensing device), a lens unit 20, two coaxial cables 30 (30A, 30B), a support 40, and solder 50.

(Solid-State Image Sensing Device)

The solid-state image sensing device 10 is, for example, a complementary metal oxide semiconductor (referred to as a CMOS), a charge coupled device (referred to as a CCD), or the like.

The solid-state image sensing device 10 has a light-receiving face 11, a terminal surface 12 located on the opposite side of the light-receiving face 11, and a terminal group G provided on the terminal surface 12. The terminal group G includes a plurality of image-sensing terminals (bump), each of which has a diameter of approximately 200 µm, that is, image-sensing terminals 13A, 13B, 14A, and 14B. In the embodiments shown in the FIGS. 1 and 2, the number of the image-sensing terminals is four, that is, two first image-sensing terminals 13A and 14A, and two second image-sensing terminals 13B and 14B are provided on the terminal surface 12.

Note that, in the configuration shown in FIG. 1, the first image-sensing terminal 14A is disposed at a position at which the first image-sensing terminal 14A overlaps the first image-sensing terminal 13A. The second image-sensing terminal 14B is disposed at a position at which the second image-sensing terminal 14B overlaps the second image-sensing terminal 13B.

(Lens Unit)

The lens unit 20 is connected to the light-receiving face 11. A lens unit such as an object lens is mounted on the lens unit 20.

(Support)

The support 40 is formed of an insulator made of a known insulation material. As the insulation material, a ceramic or a resin is adopted. Moreover, for example, a sintered material such as alumina or LTCC may be used. In addition, as a material used to form the insulator, for example, a glass epoxy substrate (FR-4), a ferrule substrate, a silicon substrate, or a glass substrate may be adopted.

The support 40 has a first end face 40T (first end), a second end face 40B (second end) located on the opposite side of the first end face 40T, and a side face 40S located between the first end face 40T and the second end face 40B. The first end face 40T is provided on the terminal surface 12 by a known adhesive or the like. The second end face 40B faces the coaxial cable 30.

The surface area of the first end face 40T is larger than the surface area of the second end face 40B. When seen in a cross-sectional view shown in FIG. 1, the support 40 has a trapezoidal shape.

Note that, as the junction structure between the support 40 and the first end face 40T, not only a structure using adhesive but also a structure in which the support 40 is mounted on the first end face 40T may be adopted; however, in terms of a reduction in the cost of manufacturing, the structure using adhesive is preferably adopted.

Furthermore, it is not limited to a tight connection structure using adhesive; connection which will be described later may be carried out in a state where the support 40 is temporarily fixed to the first end face 40T.

A guide is provided on the side face 40S. In the embodiments shown in FIGS. 1 and 2, as the guide, a plurality of grooves 41A, 41B, 42A, and 42B are provided on the side face 40S. In the embodiments shown in FIGS. 1 and 2, the number of the grooves corresponds to the number of image-sensing terminals and is therefore four. Two grooves 41A and 42A (first groove) are disposed at positions corresponding to two first image-sensing terminals 13A and 14A, respectively. Two grooves 41B and 42B (second groove) are disposed at positions corresponding to two second image-sensing terminals 13B and 14B.

Note that, in the structure shown in FIG. 1, the groove 42A is disposed at a position at which the groove 42A overlaps the groove 41A, and the groove 42B is disposed at a position at which the groove 42B overlaps the groove 41B.

When seen in a plan view in a vertical direction of the second end face 40B, the support 40 is formed in a crisscross shape. As the support 40 has a crisscross shape, it is possible to reliably prevent short-circuiting between the two image-sensing terminals adjacent to each other.

As shown in FIG. 2, a metal film 43 (conductive portion) is provided on a surface of the support 40 in the inside of each of the grooves 41A, 41B, 42A, and 42B of the support 40. As a material of the metal film 43, copper which is known as a metal having a high degree of electroconductivity is used.

A conductor (internal conductor, external conductor) of the coaxial cable 30 (30A, 30B) which will be described later is disposed in the inside of each of the grooves 41A, 41B, 42A, and 42B. Since the conductor can move inside the groove in the extending direction of the groove, the support 40 functions as a guide member that guides the conductor.

By reducing a height of the support 40 in the Z-direction, that is, by shortening the distance from the first end face 40T to the second end face 40B, a rigid portion length of the imaging module 1 can be shortened, and it contributes to reduction in size of the imaging module 1.

Inside the grooves 41A, 41B, 42A, and 42B, the solder 50 electrically connects the conductor of the coaxial cable 30 to an image-sensing terminal corresponding to the conductor.

Inside the groove 41A, an internal conductor 31A is disposed so as to extend in a direction in which the groove 41A extends. Inside the groove 41A, the metal film 43, the image-sensing terminal 13A, and the internal conductor 31A are electrically connected to each other by the solder 50.

Inside the groove 41B, an external conductor 33A is disposed so as to extend in a direction in which the groove 41B extends. Inside the groove 41B, the metal film 43, the image-sensing terminal 13B, and the external conductor 33A are electrically connected to each other by the solder 50.

Inside the groove 42A, an internal conductor 31B is disposed so as to extend in a direction in which the groove 42A extends. Inside the groove 42A, the metal film 43, the image-sensing terminal 14A, and the internal conductor 31B are electrically connected to each other by the solder 50.

Inside the groove 42B, an external conductor 33B is disposed so as to extend in a direction in which the groove 42B extends. Inside the groove 42B, the metal film 43, the image-sensing terminal 14B, and the external conductor 33B are electrically connected to each other by the solder 50.

As shown in FIG. 1, the grooves 41A (42A) and the groove 41B (42B) are disposed axisymmetrically with respect to the center line CL. Here, the center line CL is the line located at the center of the support 40 in the direction orthogonal to the first end face 40T (Z-direction).

The groove 41A (42A) extends in the inclination direction K1 oblique to the center line CL. The groove 41B (42B) extends in the inclination direction K2 oblique to the center line CL. The internal conductor 31A and the external conductor 33A are split from the coaxial cable 30A in a Y-shape. Similarly, the internal conductor 31B and the external conductor 33B are split from the coaxial cable 30B in a Y-shape.

On the side face 40S on which the grooves are not formed, a width of the side face 40S in the direction orthogonal to the center line CL gradually decreases in a direction from the first end face 40T to the second end face 40B. Particularly, the width W1 of the side face 40S at the position close to the first end face 40T is larger than the width W2 of the side face 40S at the position close to the second end face 40B.

For this reason, the extending directions of the internal conductor 31A and the external conductor 33A which are split in a Y-shape can coincide with the inclination direction K1 of the groove 41A and the inclination direction K2 of the groove 41B, respectively.

Consequently, since the internal conductor 31A and the external conductor 33A linearly extend from the portion that is split from the coaxial cable 30A, it is possible to minimize the number of the portions at which the conductors are bent.

(Signal Cable)

Figure 3:
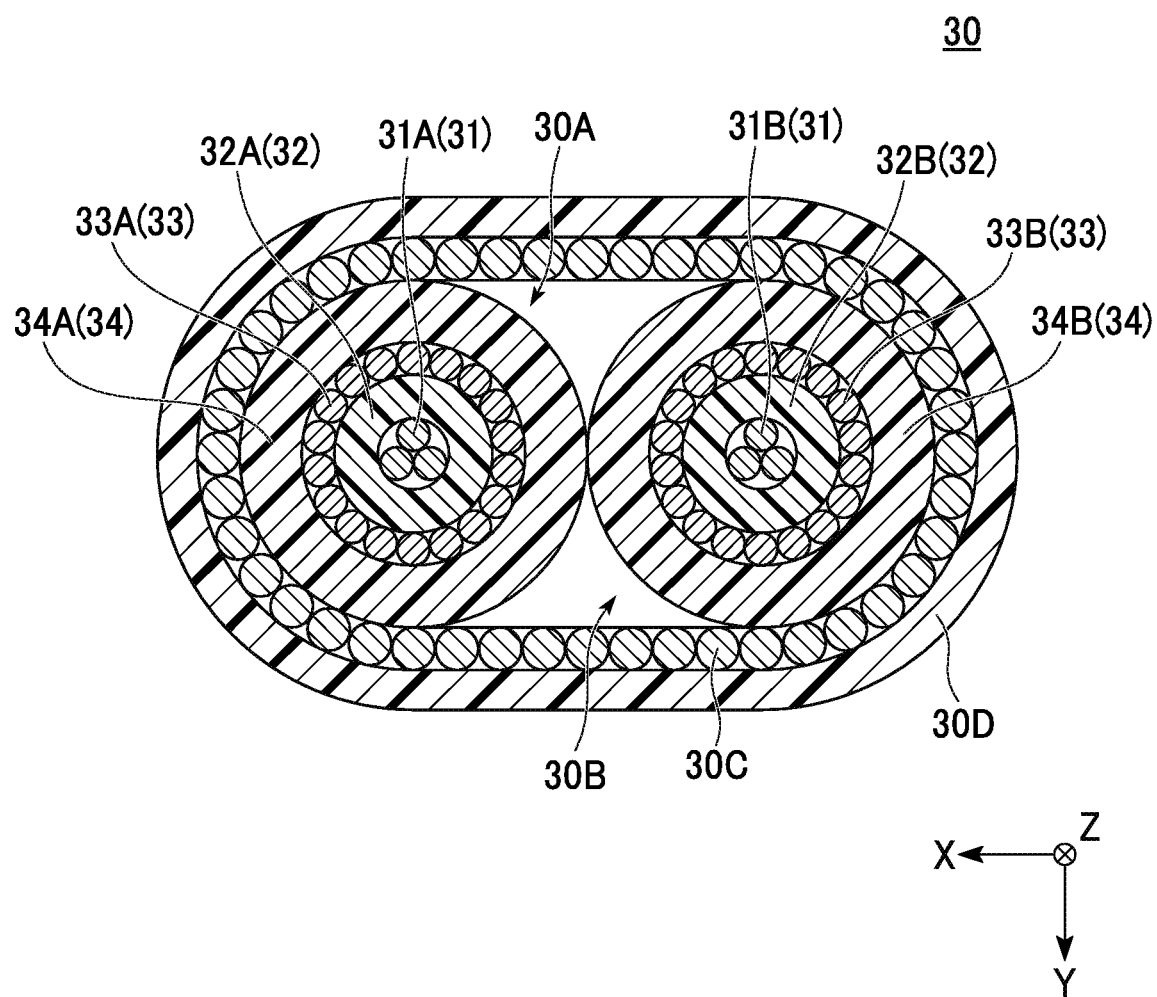
FIG. 3 is a cross-sectional view showing a signal cable which constitutes the imaging module according to one or more embodiments of the invention.

As shown in FIG. 3, the coaxial cable 30 includes two coaxial cables (a first coaxial cable 30A and a second coaxial cable 30B), a shield conductor 30C that surrounds the first coaxial cable 30A and the second coaxial cable 30B, and an outer coating 30D that surrounds the shield conductor 30C. The shield conductor 30C is provided on the entire inner peripheral surface of the outer coating 30D and is formed in a layer shape.

Each of the coaxial cables 30A and 30B includes an internal conductor 31 (31A, 31B), an internal insulator 32 (32A, 32B, conductor), an external conductor 33 (33A, 33B, conductor), and an external insulator 34 (34A, 34B). The external conductor 33 (33A, 33B) is disposed so as to cover the outside of the internal conductor 31 (31A, 31B).

For example, the internal conductor 31 is used as a signal line that supplies a signal to the solid-state image sensing device 10, and the external conductor 33 is used as a power supply line that supplies electric power to the solid-state image sensing device 10.

(Connection of the Internal Conductor and the External Conductor with Respect to Image-Sensing Terminal)

Next, a method of connecting the internal conductor 31 and the external conductor 33 to the image-sensing terminals 13A, 13B, 14A, and 14B will be described with reference to FIG. 2.

Firstly, the first end face 40T of the support 40 is adhesively attached to the terminal surface 12 of the solid-state image sensing device 10 by use of a known adhesive. At this time, the adhesive attachment is carried out so that the image-sensing terminals 13A, 13B, 14A, and 14B are disposed inside the grooves 41A, 41B, 42A, and 42B, respectively.

Next, the internal conductor 31A is disposed inside the groove 41A as shown by reference letter A, the external conductor 33A is disposed inside the groove 41B as shown by reference letter B, the internal conductor 31B is disposed inside the groove 42A as shown by reference letter C, and the external conductor 33B is disposed inside the groove 42B as shown by reference letter D.

Because of this, the positions of the internal conductors 31A and 31B and the external conductors 33A and 33B with respect to the image-sensing terminals 13A, 13B, 14A, and 14B are determined. Since the above-described positional alignment of the internal conductor and the external conductor is carried out by the grooves 41A, 41B, 42A, and 42B, the positions of the internal conductors and the external conductors coincide with the positions of the image-sensing terminals, and the internal conductors and the external conductors are prevented from being displaced from the grooves.

Furthermore, in a state where the internal conductor or the external conductor is disposed inside the groove, a position of the internal conductor or a position of the external conductor is adjusted in the extending direction of the groove, that is, it is possible to move the internal conductor or the external conductor. Since the support 40 provided with the groove (guide) functions as a guide member that guides the internal conductor or the external conductor, it is possible to move the internal conductor or the external conductor so as to approach the image-sensing terminal or move them away from the image-sensing terminal. Accordingly, it is possible to adjust the shape of the connection structure formed by the solder 50, the image-sensing terminals, and the internal conductor (external conductor) inside the groove depending on the temperature or the amount of coating of the solder 50 in a molten state (a liquid state).

Next, the solder 50 is melted by use of a soldering iron, and therefore electrical connection is carried out by the solder 50. Here, the support 40 is used as a base that stabilizes the position of the soldering iron. That is, the electrical connection is carried out by the solder 50 in a state where part of the soldering iron is in contact with the support 40. Specifically, in a state where the positions of the internal conductor and the external conductor with respect to the image-sensing terminals are determined, while melting the solder 50 by use of the soldering iron, the image-sensing terminal 13A is electrically connected to the internal conductor 31A, the image-sensing terminal 13B is electrically connected to the external conductor 33A, the image-sensing terminal 14A is electrically connected to the internal conductor 31B, and the image-sensing terminal 14B is electrically connected to the external conductor 33B. As a result, shown in FIG. 1, the imaging module 1 is obtained.

Note that, if the internal conductor and the external conductor can be electrically connected to the image-sensing terminals, the internal conductor or the external conductor may be disposed so as to be separated from the image-sensing terminals. In this case, since the solder 50 or the metal film 43 is present between the internal conductor and image-sensing terminal and between the external conductor and the image-sensing terminal, the electrical connection of the internal conductor and the external conductor with respect to the image-sensing terminals is obtained.

According to one or more embodiments, it is possible to carry out connection operation in a state where the positions of the internal conductor and the external conductor are determined by the grooves 41A, 41B, 42A, and 42B which function as the guide and in a state where the soldering iron is stabilized by the support 40. Consequently, it is possible to easily connect the internal conductor or the external conductor to the image-sensing terminal having a fine diameter such as approximately 200 μm.

Additionally, the metal film 43 (conductive portion) is formed inside each of the grooves 41A, 41B, 42A, and 42B of the support 40. Since the electrical connection is carried out by use of the solder 50 so as to coat the metal film 43 when the internal conductor or the external conductor is connected to the image-sensing terminal, the bonding surface area of the image-sensing terminal with respect to the internal conductor and the external conductor increases, and therefore the reliability of electrical connection can be improved.

The metal film 43 has a high degree of wettability (liquid-affinity) with respect to the solder 50 in a molten state (a liquid state). For this reason, when the electrical connection is carried out by the solder 50, it is possible to concentrate melted solder 50 on the metal film 43. As a result, it is possible to further improve the connection reliability obtained by the solder 50.

Moreover, in the case where the support 40 is formed of ceramic, the ceramic is exposed at portions at which the metal film 43 is not formed. In addition, the ceramic has hydrophobicity with respect to the solder 50 in a molten state (a liquid state). For this reason, in the case where the molten solder is applied to the exposed portion formed of ceramic, the molten solder flows to the metal film 43 having liquid-affinity from the ceramic exposed area having hydrophobicity. Due to a difference in liquid-affinity between the ceramic exposed area and the metal film 43, the flowability of the molten solder toward the metal film 43 increases, and the electrical connection is carried out by use of the solder 50 so as to coat the metal film 43. Accordingly, the bonding surface area of the image-sensing terminal with respect to the internal conductor and the external conductor increases, and therefore the reliability of electrical connection can be improved.

Note that, in one or more embodiments discussed so far, the configuration is described in which the metal film 43 is formed inside each of the grooves 41A, 41B, 42A, and 42B of the support 40, but the invention is not limited to this configuration. A configuration that does not include the metal film 43 may be adopted. Even in this case, since the positions of the internal conductor and the external conductor are aligned by each of the grooves 41A, 41B, 42A, and 42B, the internal conductor and the external conductor can be prevented from being displaced from the positions of the image-sensing terminals.

Next, additional embodiments of the invention will be described with reference to FIGS. 4 and 5.

Figure 4:
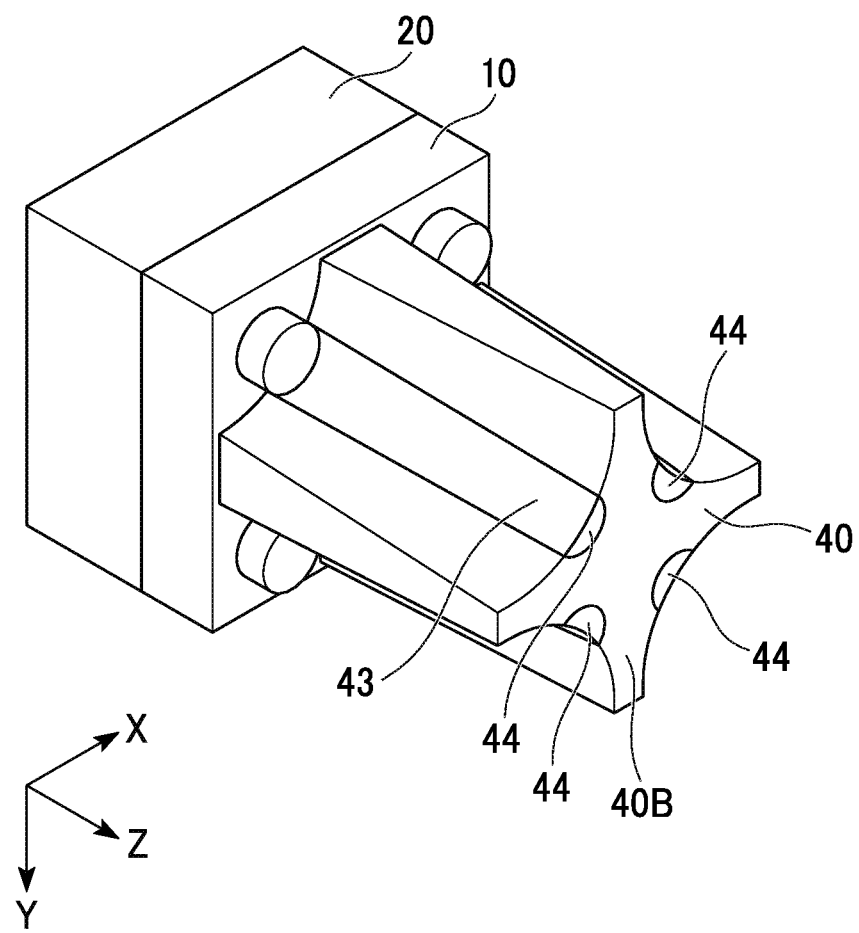
FIG. 4 is an enlarged perspective view showing a solid-state image sensing device and a support which constitute an imaging module according to one or more embodiments of the invention and is a view showing a state before the coaxial cable is connected to the support.
Figure 5:
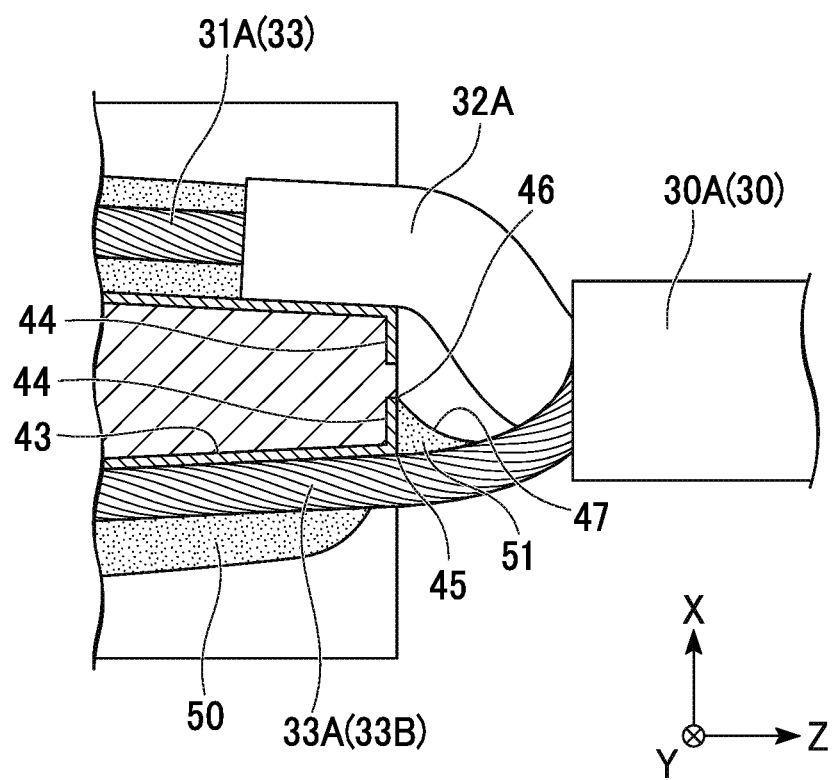
FIG. 5 is an enlarged cross-sectional view partially showing a connection structure of the support and a signal cable which constitute the imaging module according to one or more embodiments of the invention.

In FIGS. 4 and 5, identical reference numerals are used for the elements which are identical to those of the above-described one or more embodiments, and the explanations thereof are omitted or simplified here.

The additional embodiments described below are different from the previously-described embodiments in that a metal film is formed on the second end face 40B.

Specifically, as shown in FIG. 4, a metal film 44 (end-face conductive portion) that is electrically conducted to the metal film 43 is provided on the second end face 40B of the support 40.

The metal film 44 has a connection portion 45 located between the metal film 43 (conductive portion) and the external conductor 33A (conductor). In addition, the metal film 44 has an end portion 46 located at a position apart from the connection portion 45.

The solder 51 has a curved surface 47 that extends from the end portion 46 toward an outside of the second end face 40B along a surface of the external conductor 33A. The solder 51 coats the metal film 44 and the connection portion 45.

According to one or more embodiments, in addition to the effects obtained by the aforementioned embodiments, the bonding surface area between the external conductor 33A and the metal film 44 on the second end face 40B increases, and therefore the reliability of electrical connection can be improved.

Note that, in the example shown in FIG. 5, although the internal conductor 31A is covered with the internal insulator 32A, the internal conductor 31A may be exposed, and the internal conductor 31A may be electrically connected to the metal film 44 by the solder 51. In this case, the bonding surface area between the internal conductor 31A and the metal film 44 increases, and therefore the reliability of electrical connection can be improved.

MODIFIED EXAMPLES

Next, modified examples of one or more embodiments of the invention will be described with reference to FIGS. 6A and 6B.

Figure 6A:
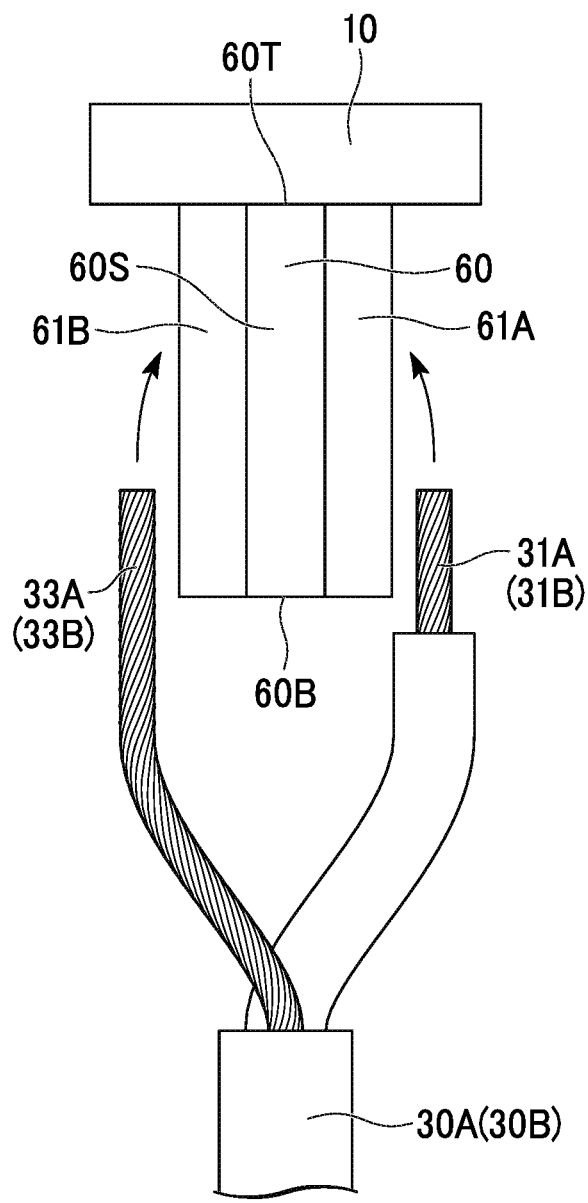
FIG. 6A is a side view partially showing the connection structure of the solid-state image sensing device, the support, and the coaxial cable which constitute the imaging module according to one or more embodiments and a modified example of one or more embodiments of the invention.
Figure 6B:
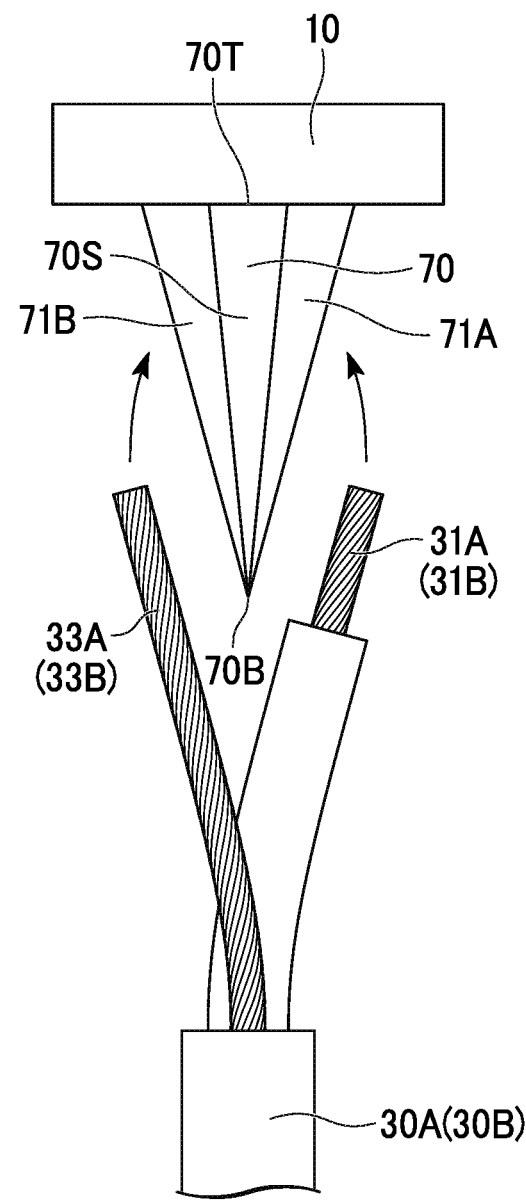
FIG. 6B is a side view partially showing the connection structure of the solid-state image sensing device, the support, and the coaxial cable which constitute the imaging module according to one or more embodiments and a modified example of one or more embodiments of the invention.

In FIGS. 6A and 6B, identical reference numerals are used for the elements which are identical to those of the embodiments which are described above, and the explanations thereof are omitted or simplified here.

The support 40 shown in FIG. 1 has a trapezoidal shape and has a configuration in which the surface area of the first end face 40T is larger than the surface area of the second end face 40B. In contrast, the modified examples shown in FIGS. 6A and 6B are different from the one or more embodiments in a shape of the support.

Modified Example 1

A support 60 shown in FIG. 6A includes a first end face 60T (first end), a second end face 60B (second end) located on the opposite side of the first end face 60T, and a side face 60S located between the first end face 60T and the second end face 60B. A groove 61A and a groove 61B are provided on the side face 60S. The surface area of the first end face 60T is the same as that of the second end face 60B. The configuration of the first end face 60T in a plan view is the same as that of the second end face 60B. That is, the support 60 has a configuration in which the groove 61A and the groove 61B are formed on the side face 60S of the insulator having a cylindrical shape. The internal conductor 31A is disposed in the groove 61A. The external conductor 33A is disposed in the groove 61B. The metal film 43 is formed on the groove 61A and the groove 61B. Note that, other configuration of the support 60 is the same as that of the support 40.

Even in the case where the above-described configuration is adopted, it is possible to obtain the same effect as that of the previously discussed one or more embodiments.

Note that, the metal film 44 that is electrically conducted to the metal film 43 may be provided on the second end face 60B.

Modified Example 2

A support 70 shown in FIG. 6B includes a first end face 70T (first end), a second end 70B located on the opposite side of the first end face 70T, and a side face 70S located between the first end face 70T and the second end 70B. A groove 71A and a groove 71B are provided on the side face 70S. The support 70 has a configuration in which the groove 71A and the groove 71B are formed on the side face 70S of the insulator having a pyramid (four-sided pyramid) shape. The internal conductor 31A is disposed in the groove 71A. The external conductor 33A is disposed in the groove 71B. The metal film 43 is formed on the groove 71A and the groove 71B. Note that, other configuration of the support 70 is the same as that of the support 40.

Even in the case where the above-described configuration is adopted, it is possible to obtain the same effect as that of the above-mentioned one or more embodiments.

Next, further embodiments of the invention will be described with reference to FIGS. 7A and 7B.

Figure 7A:
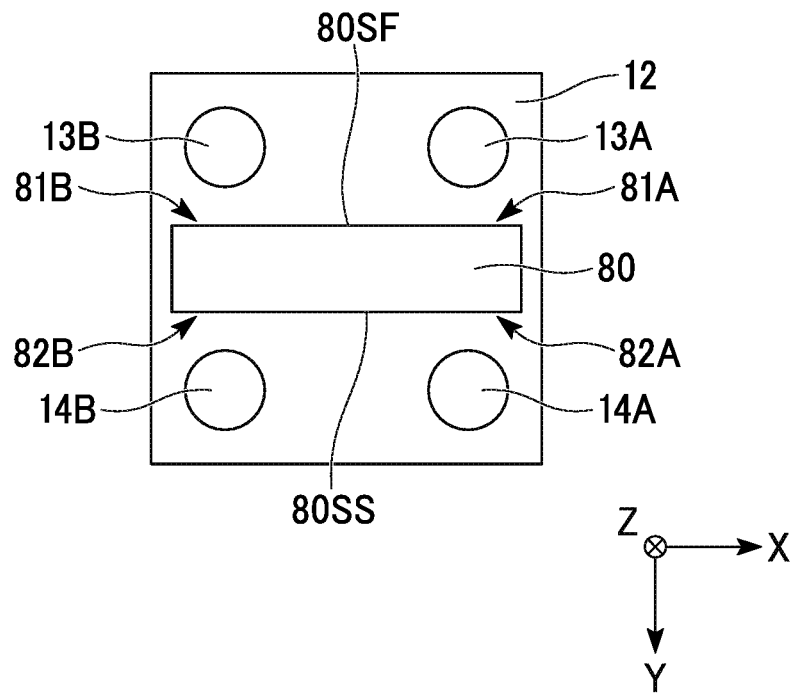
FIG. 7A is a plan view showing a solid-state image sensing device and a support which constitute the imaging module according to one or more embodiments of the invention and a modified example thereof and is an explanatory diagram showing a relative positional relationship between a solid-state image sensing device and a support.
Figure 7B:
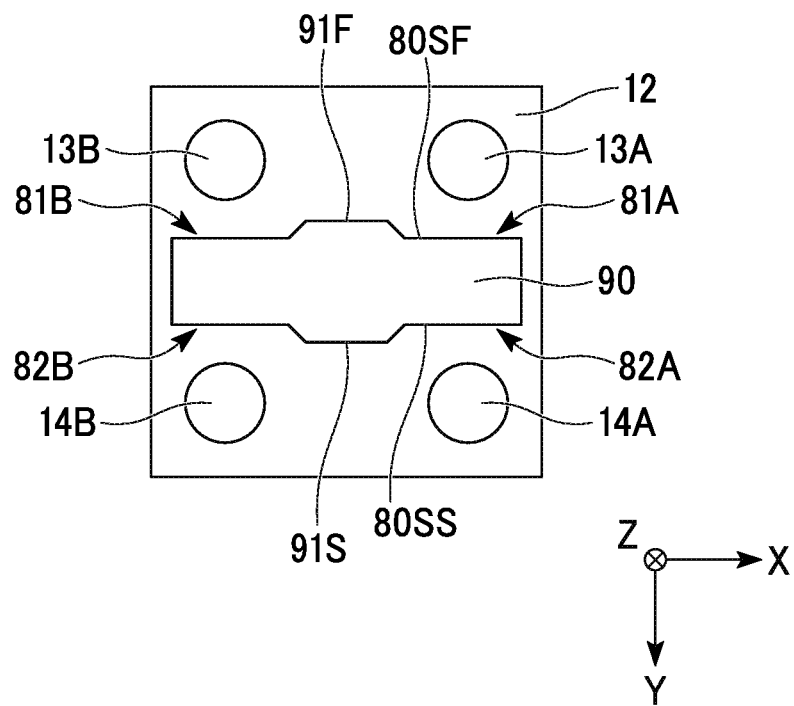
FIG. 7B is a plan view showing a solid-state image sensing device and a support which constitute the imaging module according to one or more embodiments of the invention and a modified example thereof and is an explanatory diagram showing a relative positional relationship between a solid-state image sensing device and a support.

In FIGS. 7A and 7B, identical reference numerals are used for the elements which are identical to those of the one or more embodiments described above, and the explanations thereof are omitted or simplified here.

The support 40 shown in FIGS. 1 and 4 has a crisscross shape in a plan view as seen in the Z-direction. In contrast, one or more embodiments shown in FIGS. 7A and 7B are different from the one or more embodiments in a shape of the support.

A support 80 shown in FIG. 7A functions as a guide member having an I-shape. The support 80 has a first side face 80SF and a second side face 80SS located on the opposite side of the first side face 80SF. A groove that functions as the guide shown in FIGS. 1, 2, 4, 6A, and 6B is not formed on the first side face 80SF and the second side face 80SS.

In contrast, in one or more embodiments, a region 81A (first region) facing the image-sensing terminal 13A and a region 81B (second region) facing the image-sensing terminal 13B which are on the first side face 80SF function as the guide. Additionally, a region 82A (first region) facing the image-sensing terminal 14A and a region 82B (second region) facing the image-sensing terminal 14B which are on the second side face 80SS function as the guide.

Particularly, when the image-sensing terminal 13A is connected to the internal conductor 31A, it is possible to electrically connect the image-sensing terminal 13A to the internal conductor 31A via the solder 50 while the region 81A is in contact with the internal conductor 31A. Moreover, when the image-sensing terminal 13B is connected to the external conductor 33A, it is possible to electrically connect the image-sensing terminal 13B to the external conductor 33A via the solder 50 while the region 81B is in contact with the external conductor 33A.

Similarly, on the second side face 80SS, while the conductors (internal conductor, external conductor) are in contact with the region 82A and the region 82B, electrical connection by the solder 50 is carried out.

In the example shown in FIG. 7A, although a groove having a surface (curved surface) having curvature is not formed, since the support 80 is disposed between two image-sensing terminals adjacent to each other, it is possible to reliably prevent short-circuiting between the two image-sensing terminals adjacent to each other. Furthermore, the metal film 43 may be formed on each of the regions 81A, 81B, 82A, and 82B. In this case, the metal film 44 that is electrically conducted to the metal film 43 may be formed on a flat surface of the support 80 shown in FIG. 7B (a surface orthogonal to the first side face 80SF and the second side face 80SS).

In particular, in the case where the metal film 43 is formed on each of the regions 81A, 81B, 82A, and 82B and the support 80 is formed of ceramic, the ceramic is exposed at portions at which the metal film 43 is not formed. In a step of melting solder and bonding conductors (internal conductor, external conductor) to the metal film 43, due to a difference in liquid-affinity between the ceramic exposed area and the metal film 43, the flowability of the molten solder toward the metal film 43 increases, and the electrical connection is carried out by use of the solder 50 so as to coat the metal film 43.

That is, even in the configuration in which a groove is not formed on a side face, it is possible to obtain the same effect as that of the above-mentioned one or more embodiments.

MODIFIED EXAMPLES

A support 90 shown in FIG. 7B is different from the support 80 shown in FIG. 7A in that protrusion is formed on each of the first side face 80SF and the second side face 80SS.

Specifically, protrusion 91F is formed at the center of the first side face 80SF. The protrusion 91F is located between the region 81A and the region 81B. Similarly, protrusion 91S is formed at the center of the second side face 80SS. The protrusion 91S is located between the region 82A and the region 82B.

In other words, in the case of focusing on a thickness of the support 90 (thickness in Y-direction), the thickness of between the protrusion 91F and the protrusion 91S is larger than the thickness between the first side face 80SF and the second side face 80SS on which the protrusions are not formed. The protrusion 91F and the protrusion 91S function as the guide.

Particularly, when the image-sensing terminal 13A is connected to the internal conductor 31A, it is possible to electrically connect the image-sensing terminal 13A to the internal conductor 31A via the solder 50 while the region 81A is in contact with the internal conductor 31A. At this time, the internal conductor 31A is prevented from moving toward the region 81B by the step difference formed between the region 81A and the protrusion 91F.

Moreover, when the image-sensing terminal 13B is connected to the external conductor 33A, it is possible to electrically connect the image-sensing terminal 13B to the external conductor 33A via the solder 50 while the region 81B is in contact with the external conductor 33A. At this time, the external conductor 33A is prevented from moving toward the region 81A by the step difference formed between the region 81B and the protrusion 91F.

Similarly, on the second side face 80SS, while the conductors (internal conductor, external conductor) are in contact with the region 82A and the region 82B, electrical connection by the solder 50 is carried out. At this time, the conductor (internal conductor, external conductor) is prevented from moving toward an adjacent region by the step difference formed by the protrusion 91S.

According to the modified examples, in addition to the effects obtained by the one or more embodiments discussed earlier, it is possible to limit the region in which the conductor (internal conductor, external conductor) moves by the protrusion 91F and the protrusion 91S.

While embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

What is claimed is:

1. An imaging module comprising:
   an image-sensing device comprising:
   a light-receiving face;
   a terminal surface located on an opposite side of the light-receiving face; and
   a plurality of image-sensing terminals provided on the terminal surface;
   a support that comprises:
   a first end disposed on the terminal surface;
   a second end disposed on an opposite side of the first end;
   a side face disposed between the first end and the second end;
   a guide disposed on the side face so as to correspond to positions of the image-sensing terminals and that is formed of an insulator;
   a coaxial cable comprising a conductor disposed on the guide; and
   solder that electrically connects the conductor to an image-sensing terminal corresponding to the conductor on the guide, wherein
   the guide of the support comprises a plurality of grooves disposed on the side face so as to correspond to the positions of the image-sensing terminals,
   the conductor of the coaxial cable is disposed inside each of the plurality of grooves,
   in the inside of each of the plurality of grooves, the solder electrically connects the conductor to one of the plurality of image-sensing terminals that corresponds to the conductor.

2. The imaging module according to claim 1, wherein the support comprises a conductive portion disposed on a surface of the guide, and
   on the guide, the solder electrically connects together the conductive portion, the image-sensing terminal corresponding to the conductor, and the conductor.

3. An imaging module comprising:
   an image-sensing device comprising:
   a light-receiving face;
   a terminal surface located on an opposite side of the light-receiving face; and
   a plurality of image-sensing terminals provided on the terminal surface;
   a support that comprises:
   a first end disposed on the terminal surface;
   a second end disposed on an opposite side of the first end;
   a side face disposed between the first end and the second end;
   a guide disposed on the side face so as to correspond to positions of the image-sensing terminals and that is formed of an insulator;
   a coaxial cable comprising a conductor disposed on the guide; and
   solder that electrically connects the conductor to an image-sensing terminal corresponding to the conductor on the guide, wherein
   the support comprises a conductive portion disposed on a surface of the guide,
   on the guide, the solder electrically connects together the conductive portion, the image-sensing terminal corresponding to the conductor, and the conductor,
   the support comprises an end-face conductive portion disposed on the second end and that is electrically connected to the conductive portion,
   the end-face conductive portion comprises:
   a connection portion disposed between the conductive portion and the conductor; and
   an end portion disposed at a position separated from the connection portion,
   the solder forms a curved surface that extends from the end portion toward an outside of the second end along a surface of the conductor, and the solder coats the end-face conductive portion and the connection portion.

4. The imaging module according to claim 1, wherein
the conductor is an internal conductor of the coaxial cable,
the coaxial cable comprises an external conductor that covers an outside of the internal conductor,
the internal conductor is disposed inside a first groove of the plurality of grooves,
the internal conductor is electrically connected to an image-sensing terminal corresponding to the first groove,
the external conductor is disposed inside a second groove of the plurality of grooves, and
the external conductor is electrically connected to an image-sensing terminal corresponding to the second groove.

5. The imaging module according to claim 4, wherein
the first groove and the second groove extend obliquely with respect to a center line orthogonal to the first end so as to be axisymmetric with respect to the center line,
the internal conductor and the external conductor are split from the coaxial cable in a Y-shape,
the internal conductor is disposed inside the first groove so as to extend along the first groove, and
the external conductor is disposed inside the second groove so as to extend along the second groove.

6. The imaging module according to claim 5, wherein
a width, in which a direction orthogonal to the center line, of the side face on which the first groove and the second groove are not provided gradually decreases in a direction from the first end to the second end.

7. An imaging module comprising:
an image-sensing device comprising:
  a light-receiving face;
  a terminal surface located on an opposite side of the light-receiving face; and
  a plurality of image-sensing terminals provided on the terminal surface;
a support that comprises:
  a first end disposed on the terminal surface;
  a second end disposed on an opposite side of the first end;
  a side face disposed between the first end and the second end;
  a guide disposed on the side face so as to correspond to positions of the image-sensing terminals and that is formed of an insulator;
a coaxial cable comprising a conductor disposed on the guide; and
solder that electrically connects the conductor to an image-sensing terminal corresponding to the conductor on the guide, wherein
the support is formed in a crisscross shape having four grooves in plan view, and
each of the four grooves functions as the guide.

8. The imaging module according to claim 1, wherein
the support is formed in an I-shape having a first side face and a second side face on an opposite side of the first side face, in plan view,
each of the first side face and the second side face has a first region and a second region, and
each of the first region and the second region functions as the guide.

9. The imaging module-according to claim 8, wherein
each of the first side face and the second side face comprises a protrusion between the first region and the second region, and
the protrusion functions as the guide.

* * * * *